United States Patent [19]

Regnat et al.

[11] Patent Number: 5,498,797
[45] Date of Patent: Mar. 12, 1996

[54] BIS(PHOSPHINOZLKOXY)BIARYL COMPOUNDS AND A PROCESS FOR THEIR PREPARATION

[75] Inventors: Dieter Regnat, Frankfurt; Hans-Jerg Kleiner, Kronberg, both of Germany

[73] Assignee: Hoechst Aktiengesellschaft, Germany

[21] Appl. No.: 338,033

[22] Filed: Nov. 14, 1994

[30] Foreign Application Priority Data

Nov. 13, 1993 [DE] Germany ............... 43 38 825.6

[51] Int. Cl.⁶ .......................... C07F 9/02
[52] U.S. Cl. .......................... 568/8
[58] Field of Search .................. 568/8

[56] References Cited

FOREIGN PATENT DOCUMENTS

87/07600 12/1987 WIPO .

Primary Examiner—Paul J. Killos
Attorney, Agent, or Firm—Connolly & Hutz

[57] ABSTRACT

The present invention relates to phosphorus compounds of the formula $$(R')_m-Ar^1-O-(CH_2)_k-P(Ar^2-(R'')_n)_2 \atop (R')_m-Ar^1-O-(CH_2)_k-P(Ar^2-(R'')_n)_2 \qquad (I)$$

in the (RS), (R) and (S) forms, in which $Ar^1-Ar^1$ is a biphenyl radical, 1-phenylnaphthyl radical or 1,1'-binaphthyl radical, each R', if present, independently of the others, is F, an alkyl or alkoxy radical each having 1 to 8 carbon atoms, m is an integer from 0 to 4, k is an integer from 1 to 4, $Ar^2$ is a phenyl radical, each R'', if present, is, independently of the others, F, Cl, $CF_3$, $SO_3H$, $SO_3$, $SO_3Me$ (Me is Li, Na, K), a dialkylamino radical having 2 to 8 carbon atoms, an alkyl or alkoxy radical each having 1 to 8 carbon atoms and n is an integer from 0 to 5, and to a process for their preparation.

24 Claims, No Drawings

BIS(PHOSPHINOZLKOXY)BIARYL COMPOUNDS AND A PROCESS FOR THEIR PREPARATION

DESCRIPTION

The present invention relates to novel bis(phosphinoalkoxy)biaryl compounds and to a process for their preparation.

Compounds containing two phosphino groups in the molecule (bidentate phosphine ligands) play an important role in a number of processes in which transition metal complexes are used as catalyst. See also A. Miyashita et al. in Tetrahedron Lett. 34, (1993), 2351 and in J. Am. Chem. Soc. 102, (1980), 7932; R. Noyori et al., Tetrahedron 40, (1984), 1245; H. Takaya, Tetrahedron Lett. 34, (1993) 1615. Examples of such processes are, for example, hydrogenation, hydroformylation and carbonylation reactions or alkylation and arylation of aromatics. Optically active bidentate phosphine ligands are also used in enantiomerically pure form as auxiliaries for carrying out enantioselectively catalyzed processes, such as, for example, shown in P. Salvadori, Synthesis 1992, 503 and U. Nagel, Angew. Chem. 105, (1993), 1099.

In view of the variety of possible uses of bidentate phosphine ligands, there is a need for novel bidentate phosphine ligands so that, on the one hand, the spectrum of their possible uses is complemented and broadened and, on the other hand, certain reactions can be carried out in a particularly favorable manner.

This object is achieved by phosphorus compounds (racemic and enantiomerically pure bidentate phosphine ligands) of the formula $$(R')_m-Ar^1-O-(CH_2)_k-P(Ar^2-(R'')_n)_2 \\ (R')_m-Ar^1-O-(CH_2)_k-P(Ar^2-(R'')_n)_2 \qquad (I)$$

in the (RS), (R) and (S) forms, in which $Ar^1-Ar^1$ is a biphenyl radical, 1-phenylnaphthyl radical or 1,1'-binaphthyl radical, each R', if present, independently of the others, is F, an alkyl or alkoxy radical each having 1 to 8 carbon atoms, m is an integer from 0 to 4, k is an integer from 1 to 4, $Ar^2$ is a phenyl or naphthyl radical, each R'', if present, is, independently of the others, F, Cl, $CF_3$, $SO_3H$, $SO_3Me$ (Me is Li, Na, K), a dialkylamino radical having 2 to 8 carbon atoms, an alkyl or alkoxy radical each having 1 to 8 carbon atoms and n is an integer from 0 to 5.

Of interest are phosphorus compounds in which

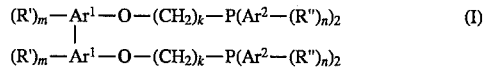 is 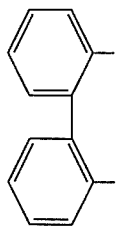

or

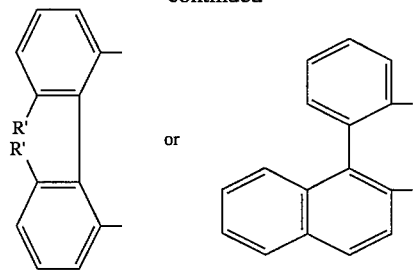

Of certain importance are phosphorus compounds in which $Ar^1-Ar^1$ is a 1,1'-binaphthyl radical and m is 0 or 1, in particular 0. k is an integer from 1 to 4, in particular 1 or 3, preferably 1. Each R'', if present, is, independently of the others, F, Cl, $CF_3$, $SO_3H$, $SO_3Me$ (Me is Li, Na, K), in particular F, $CF_3$ or an alkyl radical having 1 to 4 carbon atoms. n is an integer from 0 to 5, in particular 0 or 1.

Each R', if present, is, independently of the others, F, an alkyl or alkoxy radical each having 1 to 8 carbon atoms.

The phosphorus compounds of the formula (I) are either present as a racemic mixture, i.e. in the (RS) form, or in enantiomerically pure or largely enantiomerically pure (R) or (S) form.

The phosphorus compounds of the formula (I) according to the invention are suitable for alkylations and arylations of aromatics, in particular for arylation of aromatics, for example for coupling halogenated aromatics with arylmagnesiumhalide compounds. The coupling of 1-bromo- 2-methylnaphthalene with a naphthalenemagnesium bromide in the presence of a Pd catalyst containing the phosphorus compounds of the formula I forms the subject matter of an application filed on the same day as the present invention (p 43 38 8264).

Without claiming to be complete, the list of phosphorus compounds of the formula (I) includes the following compounds:

(RS)-2,2'-bis(diphenylphosphinomethoxy)-1,1'-binaphthyl
(R)-2,2'-bis(diphenylphosphinomethoxy)-1,1'-binaphthyl
(S)-2,2'-bis(diphenylphosphinomethoxy)-1,1'-binaphthyl
(RS)-2,2'-bis[(di-2-tolylphosphino)methoxy]-1,1'-binaphthyl
(R)-2,2'-bis[(di-2-tolylphosphino)methoxy]-1,1'-binaphthyl
(S)-2,2'-bis[(di-2-tolylphosphino)methoxy]-1,1'-binaphthyl
(RS)-2,2'-bis[(di-4-tolylphosphino)methoxy]-1,1'-binaphthyl
(R)-2,2'-bis[(di-4-tolylphosphino)methoxy]-1,1'-binaphthyl
(S)-2,2'-bis[(di-4-tolylphosphino)methoxy]-1,1'-binaphthyl
(RS)-2,2'-bis[(di-4-methoxyphenylphosphino)methoxy]-1,1'-binaphthyl
(R)-2,2'-bis[(di-4-methoxyphenylphosphino)methoxy]-1,1'-binaphthyl
(S)-2,2'-bis[(di-4-methoxyphenylphosphino)methoxy]-1,1'-binaphthyl
(RS)-2,2'-bis[(di-4-fluorophenylphosphino)methoxy]-1,1'-binaphthyl
(R)-2,2'-bis[(di-4-fluorophenylphosphino)methoxy]-1,1'-binaphthyl
(S)-2,2'-bis[(di-4-fluorophenylphosphino)methoxy]-1,1'-binaphthyl
(RS)-2,2'-bis[2- diphenylphosphinoethoxy]-1,1'-binaphthyl
(R)-2,2'-bis(2-diphenylphosphinoethoxy]-1,1'-binaphthyl
(S)-2,2'-bis(2-diphenylphosphinoethoxy]-1,1'-binaphthyl
(RS)-2,2'-bis(3-diphenylphosphinopropoxy]-1,1'-binaphthyl
(R)-2,2'-bis(3-diphenylphosphinopropoxy]-1,1'-binaphthyl
(S)-2,2'-bis(3-diphenylphosphinopropoxy]-1,1'-binaphthyl (RS)-6,6'-difluoro-2,2'-bis(diphenylphosphinomethoxy)biphenyl
(R)-6,6'-difluoro-2,2'-bis(diphenylphosphinomethoxy)biphenyl
(S)-6,6'-difluoro-2,2'-bis(diphenylphosphinomethoxy)biphenyl
(RS)-3,3',5,5'-tetra-tert-butyl-2,2'-bis(diphenylphosphinomethoxy)biphenyl.

The invention furthermore relates to phosphorus compounds (IV) of the formula

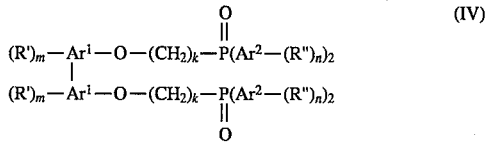

in the (RS), (R) and (S) forms, in which R', m, Ar¹—Ar¹, Ar², R" and n have the abovementioned meaning. The phosphorus compounds of the formula (IV) can successfully be used for extracting metal ions from aqueous solutions.

Without claiming to be complete, the list of phosphorus compounds of the formula (IV) includes the following compounds:
(RS)-2,2'-bis(diphenylphosphinylmethoxy)-1,1'-binaphthyl
(R)-2,2'-bis(diphenylphosphinylmethoxy)-1,1'-binaphthyl
(S)-2,2'-bis(diphenylphosphinylmethoxy)-1,1'-binaphthyl
(RS)-2,2'-bis[(di-2-tolylphosphinyl)methoxy]-1,1'-binaphthyl
(R)-2,2'-bis[(di-2-tolylphosphinyl )methoxy]-1,1'-binaphthyl
(S)-2,2'-bis[(di-2-tolylphosphinyl)methoxy]-1,1'-binaphthyl
(RS)-2,2'-bis[(di-4-tolylphosphinyl)methoxy]-1,1'-binaphthyl
(R)-2,2'-bis[(di-4-tolylphosphinyl)methoxy]-1,1'-binaphthyl
(S)-2,2'-bis[(di-4-tolylphosphinyl)methoxy]-1,1'-binaphthyl
(RS)-2,2'-bis[(di-4-methoxyphenylphosphinyl)methoxy]-1,1'-binaphthyl
(R)-2,2'-bis[(di-4-methoxyphenylphosphinyl)methoxy]-1,1'-binaphthyl
(S)-2,2'-bis[(di-4-methoxyphenylphosphinyl)methoxy]-1,1'-binaphthyl
(RS)-2,2'-bis[(di-4-fluorophenylphosphinyl)methoxy]-1,1'-binaphthyl
(R)-2,2'-bis[(di-4-fluorophenylphosphinyl)methoxy]-1,1'-binaphthyl
(S)-2,2'-bis[(di-4-fluorophenylphosphinyl)methoxy]-1,1'-binaphthyl
(RS)-2,2'-bis[2-diphenylphosphinylethoxy]-1,1'-binaphthyl
(R)-2,2'-bis[2-diphenylphosphinylethoxy]-1,1'-binaphthyl
(S)-2,2'-bis[2-diphenylphosphinylethoxy]-1,1'-binaphthyl
(RS)-2,2'-bis[3-diphenylphosphinylpropoxy]-1,1'-binaphthyl
(R)-2,2'-bis[3-diphenylphosphinylpropoxy]-1,1'-binaphthyl
(S)-2,2'-bis[3-diphenylphosphinylpropoxy]-1,1'-binaphthyl
(RS)-6,6'-difluoro-2,2'-bis(diphenylphosphinylmethoxy)biphenyl
(R)-6,6'-difluoro-2,2'-bis(diphenylphosphinylmethoxy)biphenyl.
(S)-6,6'-difluoro-2,2'-bis(diphenylphosphinylmethoxy)biphenyl
(RS)-3,3',5,5'- tetra- tert-butyl -2,2'-bis(diphenylphosphinylmethoxy)biphenyl.

The present invention furthermore provides a process for preparing the phosphorus compounds of the formula (I) and (IV). It comprises reacting a compound (II) of the formula

in the (RS), (R) or (S) forms, in which R', m and Ar¹—Ar¹ have the abovementioned meaning, with a compound (III) of the formula

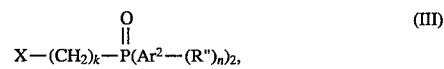

in which k, Ar², R" and n have the abovementioned meaning and X is Cl, Br, I, a rosylate, trifluoromethanesulfonate, mesylate or fluorosulfonate group, with the addition of a proton-abstracting agent and in the presence of a solvent to give the compound (IV) of the formula

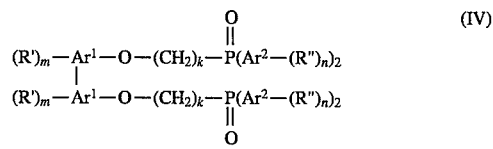

and then reducing the compound (IV).

The process according to the invention makes it possible to prepare not only the novel bis(phosphine oxides) (IV) but also the novel bis(phosphinoalkoxy)biaryls (I) in a simple manner. The advantage of the process is that the dihydroxybiaryl compounds of the formula (II) required as starting materials are readily available [R. Pummerer et al., Chem. Ber., 59 B (1926) 2159 to 2175; K. Kushioka, J. Org. Chem., 49 (1984) 4456 to 4459] and can partly also be made available in amounts on an industrial scale. Synthesis of the his(phosphinoalkoxy)biaryls proceeds in two steps via the bis(phosphine oxides) (II). Each of these two steps produces the value product desired in each case in high yield. Compounds of the formula (IV) and (I) are unexpectedly stable under the reaction conditions. Thus, surprisingly, even if workup is carried out in the presence of concentrated sodium hydroxide solution, no cleavage of the O—(CH₂)ₖ—P— group is observed.

A further advantage of the process according to the invention is that it provides not only racemic mixtures of the bis(phosphine oxides) (IV) and of the bis(phosphinoalkoxy)biaryls (I) but also, starting from enantiomerically pure or largely enantiomerically pure dihydroxybiaryl compounds (I), these compounds of the formula (I) and (IV) in enantiomerically pure or in largely enantiomerically pure form.

To obtain enantiomerically pure or in largely enantiomerically pure diphosphines or diphosphine oxides, it is usually necessary to subject their racemic mixtures to resolution (R. Noyori, J. Org. Chem., 51 (1986) 629). However, it is known that such resolutions of the racemates are usually very complicated and are frequently unsuccessful.

The process according to the invention opens up a direct synthetic route to enantiomerically pure or largely enantiomerically pure bis(phosphine oxides) (IV) and diphosphines of the formula (I) without the need for carrying out a resolution of racemates which is complicated and uncertain as to whether it will be successful. This route represents a substantial simplification compared with the conventional methods.

Compound (II) is usually reacted in the (RS), (R) or (S) formwith at least a stoichiometric amount of the proton-abstracting agent in a polar aprotic solvent or in a nonpolar solvent and with 2 to 5 equivalents of compound (III), relative to compound (II). Suitable polar aprotic solvents are tetrahydrofuran or dioxane, in particular dioxane. Suitable nonpolar solvents are toluene, oxylene, m-xylene, p-xylene, technical grade mixtures of isomeric xylenes, ethylbenzene or mesitylene, in particular toluene or technical grade mixtures of isomeric xylenes.

In a number of cases, it has proven useful to react compound (II) with 2 to 2.5 equivalents of compound (III). The proton-abstracting agent used is a strong base. Suitable bases are compounds of the formula R'''—M, in which R''' is H, an alkyl radical having 1 to 10 carbon atoms, an amide radical $NR_2''''(R''''$ is H, $C_{1-10}$-alkyl) and M is Li, Na, K or Cs or an alkali metal hexaalkyldisilazide.

Highly suitable proton-abstracting agents are sodium hydride, potassium hydride, n-butyllithium, methyllithium, tert-butyllithium, sodium amide, lithium tetramethylpiperidide, lithium diisopropylamide and/or lithium hexamethyldisilazide, in particular sodium hydride, sodium amide, preferably sodium hydride.

The preparation of the phosphorus compounds of the formula (IV) is effected by reacting the hydroxyaryl compounds (II) with the proton-abstracting agent by first introducing the deprotonated compound to which, if desired, a solvent has been added, and adding compound (III) to this solution or this suspension. However, it is also possible first to introduce compound (III) to which, if desired, a solvent has been added, and to add the deprotonated compound to which, if desired, a solvent has been added, to the solution or suspension.

Compound (II) and proton-abstracting agent are reacted in a ratio of 1:(2 to 3), in particular 1:(2 to 2.2), at −20° to 100° C., in particular 25° to 80° C. to give a correspondingly deprotonated compound. The process is particularly easy to carry out if compound (II) is reacted with sodium hydride in xylene at 25° to 50° C. This is followed by reacting the deprotonated compound with compound (III) in a ratio of 1:(1.8 to 2.5), in particular 1:(2.0 to 2.2) at 25 to 180, in particular 60° to 160° C., to give compound (IV).

Compound (IV) is then reduced in an aprotic solvent to give compound (I). Suitable aprotic solvents are toluene, o-xylene, m-xylene, p-xylene, technical grade mixtures of isomeric xylenes, dioxane, acetonitrile, in particular toluene, a xylene or industrial grade mixtures of isomeric xylene. Compound (IV) can be easily reduced with trichlorosilane. In a number of cases, it is helpful to reduce compound (IV) in the presence of a base. The base used in the reduction step is a trialkylamine, in particular triethylamine.

If desired, not only the reaction but also the reduction can be carried out under a protective inert gas atmosphere. This may have a beneficial effect on the reaction in that, for example, an increased yield is obtained. The examples which follow document the invention without limiting it.

EXPERIMENTAL SECTION

EXAMPLE 1

(RS)-2,2'-Bis(diphenylphosphinylmethoxy)-1,1'-binaphthyl

First 1.5 g (0.05 mol) of an 80% suspension of sodium hydride in paraffin oil are introduced into 100 ml of o-xylene in the absence of air and moisture, and 7.16 g (0.025 mol) of 1,1'-bi-2-naphthol are added. The mixture is heated at 50° C. for 2 hours, and 14.8 g (0.05 mol) of bromomethyldiphenylphosphine oxide are then added. The mixture is refluxed for 3 hours, cooled to 25° C., and the solid is filtered off. It[1] is digested with 100 ml of ethyl acetate and extracted with 100 ml of water. The organic phase is dried with magnesium sulfate and concentrated to give 17 g of a beige solid and, after recrystallization from ethyl acetate, 15.2 g (85%) of colorless crystals of melting point 251.5°–253° C.

| $C_{46}H_{36}O_4P_2$ | (714.74) | | | |
| --- | --- | --- | --- | --- |
| Calculated: | | C 77.3% | H 5.1% | P 8.7% |
| Found: | | C 77.2% | H 5.2% | P 8.7% |

$^{31}$P NMR: δ (CDCl$_3$) = 25.9 ppm

EXAMPLE 2

(RS)-2,2'-Bis(diphenylphosphinomethoxy)-1,1'-binaphthyl

First 15.8 g (0.022 mol) of 2,2'-bis(diphenylphosphinylmethoxy)- 1,1'-binaphthyl, 10.6 g (0.105 mol) of triethylamine are introduced into 150 ml of degassed toluene in the absence of air and moisture, and 13.5 g (0.10 mol) of trichlorosilane are added dropwise. The mixture is heated at 100° to 105° C. for 8 hours with stirring, cooled to 0° C., and 100 ml of 32% degassed sodiumhydroxide solution are then added, the phases are separated, the organic phase is dried with magnesium sulfate and concentrated to give 14.9 g of a pale yellow solid and, after crystallization with degassed acetone, 13.7 g (91%) of colorless crystals of melting point 153°–154° C.

$^{31}$P NMR: δ(CDCl$_3$)=−15.5 ppm

EXAMPLE 3

(R)-2,2'-Bis(diphenylphosphinylmethoxy)-1,1'-binaphthyl (R)-1,1'-bi-2-naphthol is reacted by the method of Example 1 to give an identical yield (85%) of (R)-2,2'-bis(diphenylphosphinylmethoxy)- 1,1'-binaphthyl having an ee of 98.5% (HPLC, chiral column)

EXAMPLE 4

(R)-2,2'-Bis(diphenylphosphinomethoxy)-1,1'-binaphthyl (R)-2,2'-bis(diphenylphosphinylmethoxy)-1,1'-binaphthyl (Example 3) is reacted by the method of Example 2 to give an identical yield (91%) of (R)-2,2'-bis(diphenylphosphinomethoxy)- 1,1'-binaphthyl having an ee of greater than 99% (HPLC, chiral column, determined after oxidizing the biphosphine to the bis(phosphine oxide) with hydrogen peroxide).

EXAMPLE 5

(RS)-3,3',5,5'-tetra-tert-butyl-2,2'-bis(diphenylphosphinylmethoxy)biphenyl

First 1.8 g (0.06 mol) of an 80% suspension of sodium hydride in paraffin oil are introduced into 200 ml of o-xylene, and 12.32 g (0.03 mol) of 3,3',5,5'-tetra-tert-butyl-2,2'-dihydroxybiphenyl are added. The mixture is heated at 100° C. for 2 hours, and 14.8 g (0.05 mol) of bromomethyldiphenylphosphine oxide are then added. The mixture is refluxed for 3 hours, cooled to 25° C., and the solid is filtered off. It is digested with 100 ml of ethyl acetate and extracted with 100 ml of water. The organic phase is dried with magnesium sulfate and concentrated to give 21.7 g of a beige solid and, after recrystallization from ethyl acetate, 19.2 g (76%) of colorless crystals of melting point

211°–212° C.

| $C_{54}H_{64}O_4P_2$ | (839.05) | | |
|---|---|---|---|
| Calculated: | C 77.3% | H 7.7% | P 7.3% |
| Found: | C 77.4% | H 7.7% | P 7.3% |

$^{31}$P NMR: δ (CDCl$_3$) = 25.87 ppm

EXAMPLE 6

3,3',5,5'-Tetra-tert-butyl-2,2'-bis(diphenylphosphinomethoxy)biphenyl

First 17.8 g (0,021 mol) of (RS)-3,3',5,5'-tetra-tertbutyl-2,2'-bis(diphenylphosphinylmethoxy)biphenyl, 10.0 g (0.10 mol) of triethylamine are introduced into 150 ml of degassed toluene, and 13.5 g (0.10 mol) of trichlorosilane are added dropwise. The mixture is heated at 100°–105° C. for 8 hours with stirring, cooled to 0° C., and 100 ml of 32% degassed sodium hydroxide solution are then added, the phases are separated, the organic phase is dried with magnesium sulfate and concentrated to give 15.3 g of a pale yellow solid and, after crystallization with degassed acetone, 14.5 g (85%) of colorless crystals of melting point 185°–187° C.

$^{31}$p NMR: δ(CDCl$_3$)=−19.6 ppm

What is claimed is:

1. A phosphorus compound of the formula $$(R')_m-Ar^1-O-(CH_2)_k-P(Ar^2-(R'')_n)_2$$
$$(R')_m-Ar^1-O-(CH_2)_k-P(Ar^2-(R'')_n)_2 \quad (I)$$

in the (RS), (R) or (S) forms or a combination, in which Ar$^1$—Ar$^1$ is a biphenyl radical, 1-phenylnaphthyl radical or 1,1'-binaphthyl radical, each R', if present, independently of the others, is F, an alkyl or alkoxy radical each having 1 to 8 carbon atoms, m is an integer from 0 to 4, k is an integer from 1 to 4, Ar$^2$ is a phenyl or naphthyl radical, each R'', if present, is, independently of the others, F, Cl, CF$_3$, SO$_3$H, SO$_3$Me (Me is Li, Na, K), a dialkylamino radical having 2 to 8 carbon atoms, an alkyl or alkoxy radical each having 1 to 8 carbon atoms and n is an integer from 0 to 5.

2. A phosphorus compound as claimed in claim 1, wherein

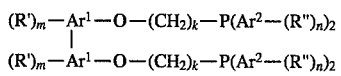
is
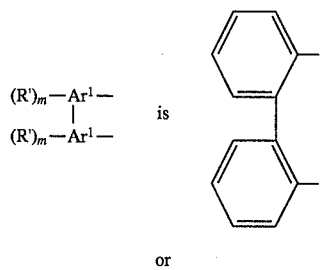
or
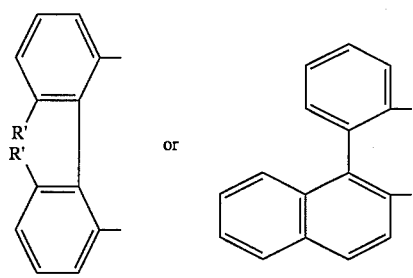

3. A phosphorus compound as claimed in claim 1, wherein Ar$^1$—Ar$^1$ is a 1,1'-binaphthyl radical and m is 0 or 1.

4. A phosphorus compound as claimed in claim 1 wherein Ar$^1$—Ar$^1$ is a 1,1'-binaphthyl radical and m is 0.

5. A phosphorus compound as claimed in claim 1, wherein k is 1 or 3.

6. A phosphorus compound as claimed in claim 1, wherein k is 1.

7. A phosphorus compound as claimed in claim 1, wherein R'' is F, CF$_3$ or an alkyl radical having 1 to 4 carbon atoms.

8. A phosphorus compound as claimed in claim 1, wherein n is 0 or 1.

9. The chemical compound 2,2'-bis(diphenylphosphinomethoxy)-1,1'-binaphthyl in the racemic or essentially pure enantiomeric (RS), (R), or (S) forms or a mixture of said forms.

10. A phosphorus compound of the formula

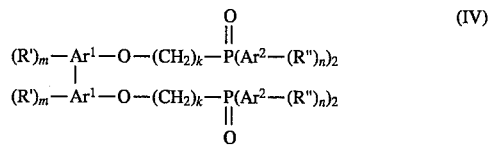

in the (RS), (R) or S forms, or a combination thereof, in which Ar$^1$—Ar$^1$ is a biphenyl radical, 1-phenylnaphthyl radical or 1,1'-binaphthyl radical, each R', if present, independently of the others, is F, an alkyl or alkoxy radical each having 1 to 8 carbon atoms, m is an integer from 0 to 4, k is an integer from 1 to 4, Ar$^2$ is a phenyl or naphthyl radical, each R'' if present, is, independently of the others, F, Cl, CF$_3$, SO$_3$H, SO$_3$Me (Me is Li, Na, K), a dialkylamino radical having 2 to 8 carbon atoms, an alkyl or alkoxy radical each having 1 to 8 carbon atoms and n is an integer from 0 to 5.

11. A process for preparing a phosphorus compound as claimed in claim or a reduced derivative 10, which comprises reacting a compound (II) of the formula

in the (RS), (R) or (S) forms, in which R', m and Ar$^1$—Ar$^1$ have the abovementioned meaning, with a compound (III) of the formula

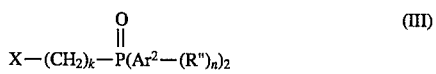

in which k, Ar$^2$, R'' and n have the abovementioned meaning and X is Cl, Br, I, a rosylate, trifluoromethanesulfonate, mesylate or fluorosulfonate group, with the addition of a proton-abstracting agent and in the presence of a solvent to give compound (IV) of the formula

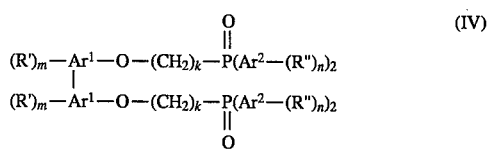

and optionally reducing compound (IV).

12. The process as claimed in claim 11, wherein compound (II) in the (RS), (R) or (S) forms is reacted with at least a stoichiometric amount of the proton-abstracting agent in a polar aprotic solvent or in a nonpolar solvent and with 2 to 5 equivalents of compound (III), relative to compound (II).

13. The process as claimed in claim 11, wherein compound (II) is reacted with 2 to 2.5 equivalents of compound (III).

14. The process as claimed in claim 11, wherein a strong base is used as the proton-abstracting agent.

15. The process as claimed in claim 11,
wherein the proton-abstracting agent used is a strong base R'''—M in which R''' is H, an alkyl radical having 1 to 10 carbon atoms, an amide radical $NR_2''''$ (R'''' is H, $C_1$- to C10-alkyl) and M is Li, Na, K or Cs, or is an alkali metal hexaalkyldisilazide.

16. The process as claimed in claim 11,
wherein the proton-abstracting agent used is sodium hydride, potassium hydride, n-butyllithium, methyllithium, tert-butyllithium, sodium amide, lithium tetramethylpiperidide, lithium diisopropylamide and/or lithium hexamethyldisilazide.

17. The process as claimed in claim 11,
wherein compound (II) and proton-abstracting agent are used in a ratio of 1=(2 to 3), at −20° to 100° C. to give a deprotonated compound.

18. The process as claimed in claim 11,
wherein compound (II) is reacted with sodium hydride in xylene at 25° to 50° C.

19. The process as claimed in claim 11, wherein a deprotonated compound, resulting from proton abstraction from a compound of formula (II), and compound (III) are reacted in a ratio of 1:(1.8 to 2.5), at 25° to 180° C.

20. The process as claimed in claim 11, wherein said optional reducing step is carried out, and wherein compound (IV) is reduced in an aprotic solvent.

21. The process as claimed in claim 11, wherein said optional reducing step is carried out, and wherein compound (IV) is reduced with trichlorosilane.

22. The process as claimed in claim 11, wherein said optional reducing step is carried out, and wherein compound (IV) is reduced in the presence of a base.

23. The process as claimed in claim 22, wherein said base is a trialkylamine.

24. The process as claimed in claim 11, wherein said optional reducing step is carried out, and wherein said reacting step and said reducing step are carried out under inert gas.

* * * * *

UNITED STATES PATENT AND TRADEMARK OFFICE
CERTIFICATE OF CORRECTION

PATENT NO. : 5,498,797
DATED : March 12, 1996
INVENTOR(S) : Dieter Regnat, et al It is certified that error appears in the above-indentified patent and that said Letters Patent is hereby corrected as shown below:

In claim 1, at column 7, line 32, please insert --thereof-- after the word "combination".

In claim 11, at column 8, the first three lines should read:

--11. A process for preparing a phosphorus compound as claimed in claim 10 or a reduced derivative thereof, which comprises reacting a compound (II) of the formula--.

In claim 11, column 8, line 45, please delete the word "rosylate" and insert the word --tosylate--.

In claim 17, column 9, line 16, please delete "1=(2 to 3)" and insert --1:(2 to 3)--.

Signed and Sealed this

Twenty-third Day of July, 1996

Attest:

BRUCE LEHMAN

*Attesting Officer*  *Commissioner of Patents and Trademarks*